(12) United States Patent
Jeng et al.

(10) Patent No.: US 7,037,516 B2
(45) Date of Patent: May 2, 2006

(54) NON-AQUEOUS SURFACTANT-CONTAINING FORMULATIONS FOR EXTENDED RELEASE OF SOMATOTROPIN

(75) Inventors: Yunhua N. Jeng, Chesterfield, MO (US); Kanaiyalal R. Patel, St. Louis, MO (US)

(73) Assignee: Monsanto Technology LLC, St. Louis, MO (US)

(*) Notice: Subject to any disclaimer, the term of this patent is extended or adjusted under 35 U.S.C. 154(b) by 221 days.

(21) Appl. No.: 10/792,992

(22) Filed: Mar. 4, 2004

(65) Prior Publication Data

US 2004/0171521 A1 Sep. 2, 2004

Related U.S. Application Data

(62) Division of application No. 09/891,445, filed on Jun. 26, 2001, now Pat. No. 6,719,992.

(60) Provisional application No. 60/214,168, filed on Jun. 26, 2000.

(51) Int. Cl.
C07K 15/00 (2006.01)

(52) U.S. Cl. ..................................... 424/422
(58) Field of Classification Search ............... None
See application file for complete search history.

(56) References Cited

U.S. PATENT DOCUMENTS

| | | | |
|---|---|---|---|
| 4,816,568 A | 3/1989 | Hamilton et al. |
| 4,857,506 A | 8/1989 | Tyle |
| 4,917,685 A | 4/1990 | Viswanathan et al. |
| 4,977,140 A | 12/1990 | Ferguson et al. |
| 5,034,229 A | 7/1991 | Magruder et al. |
| 5,037,420 A | 8/1991 | Magruder et al. |
| 5,096,885 A | 3/1992 | Pearlman et al. |
| 5,219,572 A | 6/1993 | Sivaramakrishnan et al. |
| 5,356,635 A | 10/1994 | Raman et al. |
| 5,359,030 A | 10/1994 | Ekwuribe |
| 5,399,489 A | 3/1995 | Krivi |
| 5,438,040 A | 8/1995 | Ekwuribe |
| 5,474,980 A | 12/1995 | Mitchell |
| 5,520,927 A | 5/1996 | Kim et al. |
| 5,607,691 A | 3/1997 | Hale |
| 5,612,315 A | 3/1997 | Pikal et al. |
| 5,631,227 A | 5/1997 | Harbour |
| 5,681,811 A | 10/1997 | Ekwuribe |
| 5,739,108 A | 4/1998 | Mitchell |
| 5,744,163 A | 4/1998 | Kim et al. |
| 5,773,588 A | 6/1998 | Owsley |
| 5,801,141 A | 9/1998 | Steber |
| 5,849,704 A | 12/1998 | S.o slashed.rensen et al. |
| 5,972,370 A | 10/1999 | Eckenhoff |
| 5,986,073 A | 11/1999 | Storrs et al. |
| 6,086,918 A | 7/2000 | Stern |
| 6,162,258 A | 12/2000 | Scarborough |

FOREIGN PATENT DOCUMENTS

| | | |
|---|---|---|
| EP | 0 216 485 | 4/1987 |
| EP | 0 278 103 A | 8/1988 |
| EP | 303 746 A1 | 2/1989 |
| EP | 0 374 120 A | 6/1990 |
| EP | 0 523 330 A1 | 1/1993 |
| EP | 0 913 177 | 5/1999 |
| JP | 3086834 | 4/1991 |
| WO | WO 89 09614 A | 10/1989 |
| WO | WO 93/12812 | 7/1993 |
| WO | WO 93/13792 | 7/1993 |
| WO | WO 93/19773 | 10/1993 |
| WO | WO 97/03692 | 2/1997 |
| WO | WO 97/29767 | 8/1997 |
| WO | WO 98/29131 | 7/1998 |
| WO | WO 00/13674 | 3/2000 |

OTHER PUBLICATIONS

Katakam, Manohar: *Use of non-ionic surfactants to stabilize recombinant human growth hormone and to develop its sustained release formulation*, Diss. Abstr. Int., vol. 57, No. 5, 1996, p. 3149.

*Primary Examiner*—Bruce R. Campell
*Assistant Examiner*—Roy Teller
(74) *Attorney, Agent, or Firm*—Grace L. Bonner; Howrey LLP

(57) ABSTRACT

The present invention provides compositions comprising biologically-active somatotropin formulated for extended release and methods of preparing and methods of using the same. These compositions comprise somatotropin, at least a first bioavailability-enhancing constituent (BEC), and a substantially non-aqueous, hydrophobic excipient, and optionally a second BEC. The first BEC is typically a surfactant (preferably a non-ionic surfactant) or a cyclodextrin compound. The optional second BEC may comprise (i) amino acids or amino acid derivatives; (ii) hydroxamate derivatives; (iii) non-reducing carbohydrates; (iv) oxo-acid salts; or (v) a mixture of two or more compounds from within the foregoing classes (i)–(iv).

16 Claims, 3 Drawing Sheets

NON-AQUEOUS SURFACTANT-CONTAINING FORMULATIONS FOR EXTENDED RELEASE OF SOMATOTROPIN

This is a divisional of application Ser. No. 09/891,445 filed Jun. 26, 2001, now U.S. Pat. No. 6,719,992 which application claims priority to Provisional Application Ser. No. 60/214,168 filed Jun. 26, 2000.

BACKGROUND OF THE INVENTION

1. Field of the Invention

The present invention relates to the field of biologically-active somatotropin compositions. More particularly, it concerns biologically-active compositions of somatotropin formulated for extended release into the bloodstream of an animal following parenteral administration, methods of preparing these compositions, and methods of using the same.

2. Technical Problem Addressed by the Invention

Although prolonged activity of some biologically active (bioactive) polypeptides can be achieved by parenterally administering only very small doses, others are required in sufficient serum concentrations and/or have such a short half-life in serum that a substantial dose must be administered to provide the desired biological effect over an extended time such as a week or longer. Somatotropins (growth hormones) are an example of such polypeptides.

To prevent undesirably rapid release into an animal's bloodstream, certain polypeptides have been parenterally administered in liquid vehicles which may optionally contain hydration retardants (antihydration agents) or in association with metals or metal compounds that further lower their solubility in body fluids. To avoid the need for unacceptably large quantities of such a vehicle, and for other reasons including superior prolonged release performance, it is advantageous to employ substantial concentrations of the polypeptide in the vehicle, e.g., as shown in U.S. Pat. No. 5,739,108 to James C. Mitchell, U.S. Pat. No. 4,977,140, assigned to Eli Lilly, U.S. Pat. No. 5,520,927, assigned to Lucky, Ltd., and U.S. Pat. No. 5,744,163, assigned to LG Chemicals Ltd. However, there has been a need to improve the efficiency with which such polypeptides are released into the animal's bloodstream in a biologically active form ("bioavailability") and/or, in some utilities, their effectiveness in providing the desired physiological response in the animal ("efficacy"). Each of these factors can substantially affect the amount of the polypeptide that must be administered to achieve the desired biological effect, and consequently, the cost of each administration. Typically, polypeptides such as somatotropins are made in prokaryotic organisms that have been transformed using recombinant DNA, such that even small quantities are very expensive to produce in the pure forms required for product safety and regulatory approval.

3. Description of Related Art

There is currently a substantial body of work which addresses the need for protein formulations which provide for extended release of biologically active polypeptides, including somatotropins. This body of work includes a number of publications describing the use of various stabilizing compounds and excipients. Furthermore, various methods of and devices for administering the bioactive compositions have also been reported in the existing art. Exemplary publications which address this technological problem include the following:

Christensen et al., WO 97/03692, discloses a formulation of growth hormone with zinc, and optionally lysine or calcium, ions. The formulation can contain an excipient such as a disaccharide, a polysaccharide, or a sugar alcohol. Growth hormone so formulated showed resistance to deamidation.

Dong et al., WO 00/13674, discloses a mechanism for timed-release of a drug. The mechanism comprises a semi-permeable walled container that houses a capsule, which capsule comprises a drug formulation, a piston, and an osmotic composition. The dosage mechanism releases the drug formulation through a passageway at a controlled rate over a period of up to 24 hours.

Ekwuribe, U.S. Pat. Nos. 5,359,030, 5,438,040, and 5,681,811 disclose a stabilized conjugated peptide complex comprising a peptide conjugatively coupled to a polymer including lipophilic and hydrophilic moieties which is suitable for both parenteral and non-parenteral administration.

Ferguson et al., U.S. Pat. No. 4,977,140, discloses a sustained release formulation comprising bovine somatotropin in a carrier comprising a wax (about 1%–20% by weight) and an oil (about 80%–99% by weight). On injecting into a dairy cow, the formulation led to greater milk production for 28 days.

Hamilton et al., U.S. Pat. No. 4,816,568, discloses compositions of animal growth hormones and stabilizers. The stabilizers are soluble in aqueous solutions, and generally are very polar. The stabilizers taught include polyols, amino acids, amino acid polymers with charged side groups at physiological pH, and choline derivatives. An aqueous formulation of the composition can be formed by (i) dispersing the stabilizer in an aqueous solution and (ii) subsequently adding the growth hormone. A solid formulation can be formed by (i) mixing the stabilizer and the growth hormone, (ii) optionally adding adjuvants, binders, etc. to the composition, and (iii) compressing the composition to form a tablet or pellet.

Kim et al., U.S. Pat. No. 5,520,927, discloses a parenterally administered, slow releasing bioactive pharmaceutical composition comprising somatotropin, at least one tocopherol compound, and a release delaying agent.

Kim et al., U.S. Pat. No. 5,744,163, discloses a formulation for the sustained release of animal growth hormone. The formulation comprises coating somatotropin containing pellets with a film of biodegradable polymer and a poloxamer.

Magruder et al., U.S. Pat. No. 5,034,229, discloses a device for delivering a beneficial agent, e.g. a growth hormone, to an animal. The device can also deliver a polyol as a viscosity modulating means.

Martin, EP 0 216 485, discloses a method of preparing growth hormones complexed with transition metals. Methods for promoting growth in animals by treating them with transition metal complexed growth hormones are also described.

Mitchell, U.S. Pat. No. 5,739,108, discloses extended-release formulations of bioactive polypeptides comprising the polypeptide at from about 10% by weight to about 50% by weight in a dispersion in a biocompatible oil. The polypeptide can be associated with a non-toxic metal or metal salt. The formulation can also comprise an antihydration agent, such as aluminum monostearate.

Pikal, et al., U.S. Pat. No. 5,612,315, discloses formulations for the parenteral administration of human growth hormone comprising human growth hormone, glycine, and mannitol. The disclosed formulations are described as providing stabilization against protein aggregation.

Raman et al., U.S. Pat. No. 5,356,635, discloses a sustained release composition comprising a biologically active agent, e.g. somatotropin; a biodegradable, amorphous carbohydrate glass matrix, throughout which the e.g. somatotropin is dispersed; and a hydrophobic substance. The amorphous carbohydrate glass matrix comprises an amorphous carbohydrate and a recrystallization retarding agent, and makes up from about 60% by weight to 90% by weight of the composition. The composition is solid down to at least about 18° C.

Raman et al., WO 93/13792, discloses an implantable device comprising a transition metal-somatotropin complex in combination with a transition metal-solubilizing substance. The transition metal can be zinc, manganese, or copper. The metal-solubilizing substance can be an amino acid. Sucrose can be used to stabilize the somatotropin. The device can comprise silicone tubing or wax.

Seely et al., WO 93/19773, discloses aqueous solutions comprising (i) a lyophilized somatotropin composition comprising somatotropin and arginine HCl and (ii) a diluent comprising EDTA, nonionic surfactant, and optionally buffer or a non-buffering agent such as sucrose or trehalose.

Sivaramakrishnan et al., U.S. Pat. No. 5,219,572, discloses a device for controlled release of macromolecular proteins, e.g. somatotropin. The device comprises a water-soluble outer capsule completely surrounding an inner compartment containing non-uniform beadlets. The beadlets comprise a wax shell which surrounds a core matrix. The core matrix comprises e.g. somatotropin and optionally excipients, stabilizers, binders, and the like, e.g. magnesium stearate or sucrose. Upon dissolution of the outer capsule in the fluid environment in an animal, the beadlets are exposed to the fluid environment, and rupture at various times after exposure.

Sørensen et al., WO 93/12812, teaches that growth hormone can be stabilized by the presence of histidine or a histidine derivative. If the growth hormone is lyophilized, the composition can also comprise a bulking agent, i.e. sugar alcohols, disaccharides, and mixtures thereof.

Sørensen et al., U.S. Pat. No. 5,849,704, discloses a pharmaceutical formulation comprising a growth hormone and histidine or a derivative of histidine as an additive or buffering substance added to provide stability against deamidation, oxidation or cleavage of the peptide bonds in the growth hormone. Also disclosed is that crystallization of growth hormone in the presence of histidine or a derivative thereof gives rise to a higher yield of crystals having higher purity than known methods.

Steber et al., EP 0 523 330 A1, discloses a compacted, indented, partially-coated, implantable composition comprising a biologically active polypeptide (e.g. somatotropin); a fat, wax, or mixture thereof; and a sugar (e.g. mono-, di-, or trisaccharides).

Storrs, et al. U.S. Pat. No. 5,986,073, discloses a method for purifying and recovering biologically active somatotropin monomers. This work is based on the discovery that somatotropin monomers and somatotropin oligomers having overlapping isoelectric points may nevertheless be separated by selective precipitation over a very narrow pH range. Undesirable impurities are removed by this process and the purified somatotropin monomers recovered are suitable for parenteral application to target animals without further purification.

Tyle, U.S. Pat. No. 4,857,506, discloses a multiple water-in-oil-in-water emulsion for the sustained release of a growth hormone. The growth hormone is dispersed in an internal aqueous phase; the internal aqueous phase is dispersed in a water-immiscible liquid or oil phase; and the water-immiscible phase is dispersed in an external aqueous phase. The internal aqueous phase can include up to 40% by weight polyol, glycol, or sugar.

Viswanathan et al., U.S. Pat. No. 4,917,685, discloses a delivery device for a stabilized animal growth hormone. The device comprises a wall which surrounds and defines a reservoir. At least a portion of the wall is porous, to allow passage of growth hormone and stabilizer. The growth hormone and stabilizer formulation is substantially that disclosed by Hamilton et al., described above.

Despite the efforts described in the publications summarized above, there is still room for significant improvement of the technology. The present invention satisfies this need by providing improved, sustained release formulation of a somatotropin which has the advantages of providing both higher and more sustained levels of somatotropin in the serum of animals treated with these formulations.

The art summarized above discloses formulations in which biologically active polypeptides (such as somatotropins) are dispersed in aqueous or non-aqueous vehicles which can be parenterally administered to animals for prolonged release of the polypeptide into the animal's bloodstream. This invention discloses novel non-aqueous formulations for such parenteral administration, in which a somatotropin ("ST") is dispersed, e.g., suspended, together with at least a first bioavailability enhancing constituent (hereinafter "BEC") which enhances the desired biological effect(s) of the ST in the animal. In a specific example, injection of dairy cattle with formulations of this invention have been found to result in unexpectedly elevated levels of serum ST in the animals, and for surprisingly prolonged periods of time, which is normally expected to result in a surprisingly increased production of milk by those cattle. In even more preferred embodiments, the compositions of this invention contain a second BEC, chemically distinguishable from the aforementioned first BEC, which further enhances the desired biological effects of the ST and, in many embodiments, provides with the first BEC a surprisingly great enhancement of those effects. In a particular embodiment of the invention, the first BEC, when used in combination with such a second BEC, prolongs the release enhances the effects of the ST to a highly unexpected extent.

SUMMARY OF THE INVENTION

This invention provides compositions of matter which, when administered parenterally to animals, e.g., warm-blooded animals such as mammals, result in higher serum levels of somatotropin ("ST"), and in many instances, for periods of time that are longer than those levels and time periods that result from similar administration of previously-available formulations containing the same dose of ST. Accordingly, these compositions of matter provide superior efficacy for inducing weight gain and /or milk production in mammals, compared with previously available formulations containing the same amount of ST. In some embodiments, the compositions of this invention are especially effective for sustaining milk production of a mammal, which has been elevated by administration of a ST, for time periods longer than those provided by the use of previously available ST formulations.

The compositions of the present invention, which include a ST and a first bioavailability-enhancing constituent (hereinafter "BEC"), enhance the "bioavailability" of the ST which, as the net result of the release, absorption, elimination, degradation and other physiological phenomena of the ST, typically results in a desired biological effect such as growth, milk production or feed efficiency (e.g., feed-to-milk conversion efficiency). This first BEC typically increases the solubility of the ST in the aqueous body fluids of the animal to be treated, and can be chosen from compounds and substances that are normally regarded as surfactants (preferably non-ionic surfactants, e.g., one or a mixture of two or more of the following: polyoxyethylene fatty acid esters, poloxamers, polyoxyethylene sorbitan fatty acid esters, tocopherol polyethylene glycol succinates and other tocopherol polyalkylene glycol esters of fatty acids containing from about 8 to about 24 carbon atoms, sugar fatty acid esters, polyoxyethylene glycerides, and polyoxyethylene vegetable oils), or from one or a mixture of cyclodextrin compounds such as, for instance, unsubstituted cyclodextrin or cyclodextrin having at least one water solubility-enhancing substituent, e.g., a hydroxyalkyl substituent, or from a mixture of such surfactant(s) and cyclodextrin compound(s). It is not clear whether the characteristics typically regarded as surfactant properties play a predominant, or even important role in the ST bioavailability-enhancing activity of such a first BEC in this invention. In some instances in which the first BEC and ST are combined prior to the ST being lyophilized or spray dried, it appears that the first BEC may function as a protectant of the activity of the ST during such processing and thus enhance the bioavailability of the ST after subsequent parenteral administration.

Optionally, and desirably in many instances, the compositions of this invention include a second BEC as mentioned hereinbefore. This second BEC can be one or a mixture of two or more of (a) an amino acid, amino acid derivative such as histidine-HCl, or an amino acid polymer, such as a polyhistidine; (b) an hydroxamate, such as suberohydrxamic acid, or an hydroxamate derivative, such as a histidine hydroxamate; (c) a non-reducing carbohydrate, such as a polyol or polyol ester; (d) a salt of an oxo-acid, such as a mixture of monobasic and diabasic sodium phosphates; or (e) imidazole or imidazole-HCl.

The present invention also includes methods for making the described compositions of matter and methods of using these compositions (for example, by parenteral administration of the compositions to animals).

DETAILED DESCRIPTION OF THE INVENTION

In various embodiments of the invention, the ST and the BEC(s) are suspended or otherwise combined in a substantially non-aqueous hydrophobic carrier (oil), yielding a formulation which is fluidly injectable at the body temperature of the animal to be injected (typically 37–39° C . for a mammal), and desirably at the ambient temperature for injection of the animal. The compositions of the instant invention may be of any viscosity which is compatible with use of the compositions in accordance with the present invention. In a preferred embodiment , the viscosity of the composition is between about 500 and about 10,000 centipoise at 141s-1. A particularly preferred carrier (vehicle) for use in the present invention is a mixture of 95% sesame oil and 5% aluminum monostearate . Other carriers that are believed to be satisfactorily useful in the invention include alpha-tocopherol acetate and mixtures of vegetable (e.g., sesame or peanut) oils and beeswax.

Unless specifically stated otherwise, percentages of constituents in compositions of the invention described herein are by weight of the composition.

According to the present invention the ST used in the formulations may be from any origin which is suitable for use with the invention, including, but not limited to, native and/or recombinant bovine, porcine, equine, or human somatotropin. The ST used may be present in an essentially pure form or may be combined with another substance (e.g., the ST used may be in the form of a zinc salt or zinc complex of ST).

The compositions of this invention which do not contain a second BEC usually contain a first BEC (or mixture of two or more first BECs) in a concentration of at least about 0.2%, more typically at least about 0.5%, generally not more than about 10%, and more commonly not more than about 5%. The compositions of this invention which do contain a second BEC normally contain a first BEC (or a mixture of two or more first BECs) in a concentration of at least 0.1%, more commonly at least about 0.2%, usually not more than about 10%, and preferably not more than about 5%.

In an alternative embodiment, where the second BEC is an amino acid, amino acid derivative, hydroxamate or hydroxamate derivative, or salt of an oxo-acid, the second BEC comprises at least about 1%, preferably, at least about 2%, by weight of the total composition. Typically, when the second BEC is an amino acid, amino acid derivative it comprises not more than about 15%, preferably, not more than about 10%, by weight, of the total composition.

According to another embodiment of the present invention, when the second BEC used is a non-reducing carbohydrate it comprises at least about 1%, preferably, at least about 3%, by weight of the total composition. Typically, when the second BEC is a non-reducing carbohydrate, it comprises not more than about 20%, preferably, not more than about 15%, by weight, of the total composition.

The present invention also provides a method of preparing the described compositions of matter. According to such an embodiment of the present invention the ST is provided as a lyophilized dry solid (for an example of preparing the lyophilized ST see U.S. Pat. No. 5,013,713, which is incorporated herein by reference), the first BEC is likewise provided as a liquid, in a paste- or wax-like state or a dry solid. In embodiments comprising both a first and a second BEC, either the first BEC, the second BEC or both the first and second BEC can be provided as liquid, in a paste- or wax-like state or a dry solids. The method for preparing these compositions of matter comprises mixing the first BEC, in a liquid state, in a paste- or wax-like state, or a dry solid, with the hydrophobic carrier, to produce a first suspension or solution, as the case may be, and then mixing the lyophilized, dry, solid ST with the first suspension to produce a second suspension. In embodiments having both a first liquid, in a paste- or wax-like state or a dry solid BEC and a second dry, solid BEC, both BECs would be mixed with the hydrophobic carrier to produce the above first suspension.

Another embodiment of the present invention provides a method for inducing improved weight gain or elevated milk production in a mammal. This method comprises injecting an ST formulation of the present invention into the target mammal.

Yet another embodiment of the present invention provides a method for sustaining the elevated milk production response in a lactating mammal. This method comprises injecting the target mammal with a biocompatible ST formulation according to the present invention, wherein the ST present in the formulation is active in the target mammal.

According to the present invention these compositions and methods may be better understood by a review of the detailed description in conjunction with the drawings, which serve to facilitate the further illustration of certain aspects and/or certain embodiments of the invention.

Definitions

The following definitions are provided in order to aid those skilled in the art to understand the detailed description of the present invention.

Throughout the specification, unless otherwise indicated, percentages of compositions are by weight and temperatures are in degrees Celsius (° C.).

As used in the specification and claims, the term "substantially non-aqueous" means essentially anhydrous or containing water in such low proportion that it does not intolerably accelerate release of the polypeptide in the animal. Although this proportion of water may vary with each composition of the invention it is most commonly less than about 2% and most typically less than about 1%.

The term "non-toxic" as used herein refers to components of compositions that are reasonably safe and/or innocuous when used in appropriate amounts and under appropriate conditions in parenteral administration of such compositions as are described herein.

The term "biologically-active" or "bioactive" polypeptide or protein (e.g. somatotropin) is used herein to describe a polypeptide or protein, which following appropriate parenteral administration to an animal, has a demonstrable effect on a biological process of that animal. The effect may be hormonal, nutritive, therapeutic, prophylactic, or otherwise, and may mimic, complement, or inhibit a naturally occurring biological process. Although there is a vast array of potentially regulatable biological activities or processes, the following are mentioned as exemplary: stimulation of growth, stimulation of lactation, stimulation of egg or offspring production, and enhancement of the efficiency of feed usage.

The term "biocompatible", as used herein, refers to substances which have no intolerable adverse effect on the somatotropin, the animal, or, in the case of animals whose products enter the food chain, the consumers of such products.

The term "POES" means polyoxyethylene stearate, the term "POE4S" means polyoxyethylene 4 stearate, and the term "POE8S" means polyoxyethylene 8 stearate where the number in the names means the approximate polymer length in oxyethylene units.

"Sustaining elevated milk production response" or "sustained elevated milk production response", as used herein, refers to the ability of lactating animals to maintain an elevated level of milk production, over a period of time, despite decreasing serum levels of somatotropin.

DESCRIPTION OF PREFERRED EMBODIMENTS

Figure 1:
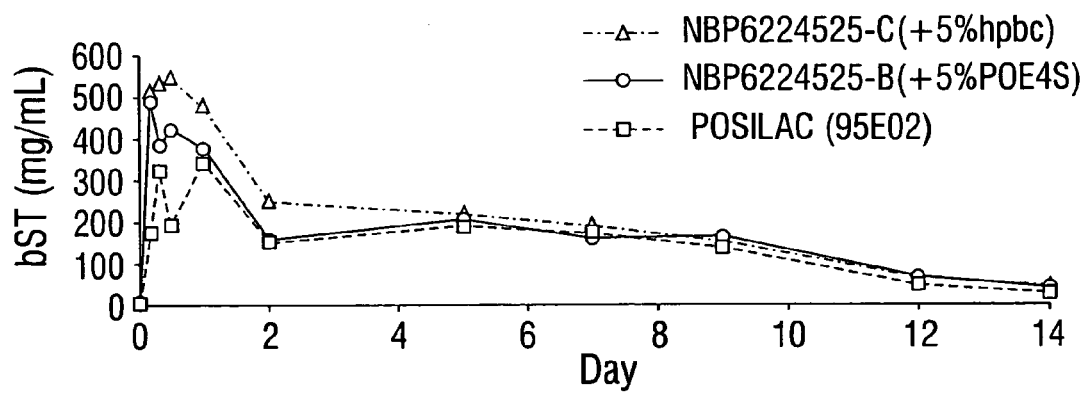
FIG. 1 is a graph showing a control treatment or example with no BEC added to the bST, and two examples measuring the serum bovine somatotropin ("bST") levels over time in rodents treated with a bST composition which contained in one example, hydroxy propyl beta cyclodextrin (or HPBC) as a bioavailability-enhancing constituent, and in the other example, polyoxyethylene 4 stearate (POE4S) as a bioavailability-enhancing constituent.

The present invention provides an injectable (or otherwise parenterally administerable) enhanced bioavailability formulation comprising: (i) a dry solid native or recombinant protein growth hormone (GH, synonymous with somatotropin, herein sometimes abbreviated as ST), and at least (ii) a first bioavailability-enhancing constituent (BEC), which may be liquid, dry and/or solid, and optionally (iii) a second bioavailability-enhancing constituent (BEC), preferably dry and/or solid. Both the ST and the first BEC are suspended in an excipient comprised of a substantially non-aqueous oil, fat, or other hydrophobic substance that is at least partially liquid to creamy and/or biodegradable in an animal at the animal's body temperature and which is biocompatible with the animal. In embodiments with a second BEC, preferably the first and second BEC are combined with each other before being introduced to the ST, however the first and second BEC and the ST may be combined in any order.

Somatotropins from man and from the common domestic animals are proteins of approximately 191 amino acids, which are synthesized and secreted by the anterior lobe of the pituitary gland. Full length human ST (hST) consists of 191 amino acids. ST is a key hormone involved in the coordination of somatic growth through the regulation of the metabolic processing of proteins, carbohydrates, and lipids. A major known effect of ST is the promotion of growth in organ systems which include, but are not limited to, the skeleton, connective tissue, muscles, and viscera such as the liver, intestine, and kidneys.

Growth hormones suitable for use in the present invention include, but are not limited to, somatotropins from human, bovine, equine, ovine, porcine, caprine, and avian sources. Preferably the ST is human, equine, bovine, or porcine ST. Even more preferably the ST is bovine or human ST (bST).

Somatotropin for use in the present invention can be obtained by extraction and subsequent concentration from the pituitary glands of various animals. Alternatively, ST may be produced using recombinant DNA techniques which are well understood and commonly used by those skilled in the art.

Somatotropins prepared using recombinant DNA techniques suitable for use according to the present invention may be produced by genetically transformed microorganism such as *E. coli*, or other bacteria, or by yeasts. Recombinant ST may also be produced by tissue culture or by a transgenic multicellular organism.

Somatotropins produced using molecular biological techniques may have an amino acid sequence identical to naturally occurring somatotropin. Alternatively, the somatotropin used may be an ST analog comprising one or more variations in amino acid sequence with respect to the native hormone. These amino acid variations may provide enhanced biological activity or some other biological or logistical advantages.

ST is usually synthesized in its native organism as an inactive precursor molecule which is processed to the mature, active form of the hormone via cleavage of an N-terminal signal peptide (26 amino acids in humans, 27 amino acids in cows). In order to express bioactive ST protein using recombinant DNA technology it may be advantageous to add, change, or delete one or more amino acids from the polypeptide. Such modifications, which do not overly diminish the activity of the ST, or make it biologically incompatible with the animal to be treated, are useful in the present invention. For example it may be useful to produce an ST polypeptide which contains a methionine residue at its N-terminus (N-terminal to the phenylalanine residue which is typically the first amino acid in the mature, active form the native hormone), resulting from microbial translation of the AUG start codon in a recombinant gene for the polypeptide (this form of ST is known as N-methionyl-ST). Another derivative envisioned for use in the present invention is N-alaninyl-ST, which is similar to N-methionyl-ST except it begins with an N-terminal alanine residue (See Krivi U.S. Pat. No. 5,399,489, which is. incorporated herein by reference) rather than an N-terminal methionine.

According to the various embodiments of the current invention the ST can administered in a chemically uncombined form. Other embodiments are advantageously carried out using ST in a form which has substantially lower solubility in aqueous environments or animal body fluids than the uncombined ST (e.g. chemically or otherwise combined with another substance). For example, the ST can be predominantly or partially chemically associated with a biocompatible metal, or an ester, amide or other moiety or moieties which aid in providing the desired bioactivity and which do not induce intolerable side effects in the animal treated with the composition. When associated with such a metal, the metal can be present as the metal per se (e.g. as a metal salt of or in a complex with the ST) or in the form of a salt or complex of the metal with one or more other anions.

Although monovalent metals (e.g. sodium or potassium) can be used advantageously in some compositions of this invention, polyvalent metals are preferred. Examples of such polyvalent metals include zinc, iron, calcium, bismuth, barium, magnesium,. manganese, aluminum, copper, cobalt, nickel, cadmium and the like. In certain highly preferred embodiments, such metal-associated ST molecules are reaction products of such metals, e.g. in ionic form, with dissolved ST. The ratio of metal to ST may vary depending on the number of active sites of the ST that associate with such metal during the formation process (e.g., it may vary as a fuiction of pH). For instance, metal may be associated with some or all negatively-charged amino acid (e.g. aspartic or glutamic) residues in the ST, or with its carboxy terminus. Some or all of the metal may be associated by any physical or chemical means including, but not limited to, as salt or complex with the ST, occluded within folds, crystals or amorphous shapes of the ST, or associated as a cation bridge between at least two ST molecules.

When the metal is polyvalent, its valence may be only partly chemically associated with the ST polypeptide in some cases, e.g. because of steric hindrance. In such cases, the remaining valence of the metal may be chemically associated with other anions. In many desirable embodiments, the metal is not chemically associated in substantial proportion with other anions that form salts or complexes having low water solubility with said metal. When the metal is partly chemically associated with other anions, such other anions (organic or inorganic) are often desirably selected from those that form water-soluble salts or complexes with that metal, e.g. $Br^-$, $Cl^-$, $I^-$, $SO_4^{2-}$, or $CH_3COO^{31}$ when the metal is zinc. Monovalent anions, e.g. $Cl^-$, are generally most preferred.

A preferred embodiment of this invention includes somatotropins associated with zinc (ZnST). In some instances, these may contain up to about 5% zinc or more, based on the weight of the somatotropin. To minimize the chance of undesirable injection site responses in the animals, however, it may be desirable for them to contain no more than about 2%, and in some instances no more than about 1% zinc. In preferred embodiments these ZnST molecules contain at least about 0.3% zinc, although lower percentages of zinc may be suitable in some cases.

Examples of other ST salts and complexes useful in this invention include: (i) acid addition salts formed with inorganic acids, e.g., hydrochloric, hydrobromic, sulfuric, phosphoric or nitric; or organic acids, e.g., acetic, oxalic, tartaric, succinic, maleic, fumaric, gluconic, citric, malic, ascorbic, benzoic, tannic, pamoic, alginic, polyglutamic, naphthalenesulfonic, naphthalene-disulfonic or polygalacturonic; (ii) salts and complexes with polyvalent organic cations, e.g. N'-dibenzylethylenediamine or ethylenediamine; and (iii) combinations of two or more of the aforementioned types of salts or complexes, e.g. zinc tannate.

Especially preferred are salts and complexes of zinc, iron, calcium, magnesium, manganese, sodium, potassium and mixtures thereof. Even more preferred, are salts or complexes of zinc, sodium or potassium, with ZnST being most preferred.

In preferred embodiments of the present invention, the first BEC comprises one or more substances selected from the following: polyoxyethylene fatty acids esters, cyclodextrins, poloxamers, polyoxyethylene sorbitan fatty acid esters, tocopherol polyethylene glycol succinates, sugar fatty acid esters, polyoxyethylene glycerides, and polyoxyethylene vegetable oils.

In other exemplary embodiments of the present invention the second BEC comprises one or more substances selected from the following: (a) an amino acid or amino acid derivative, (b) an hydroxamate or hydroxamate derivative, (c) a non-reducing carbohydrate, (d) an oxo-acid salt, or (e) imidazole or imidazole-HCl.

Amino acids and amino acid derivatives which are compatible with and preferred as a second BEC for use with the instant invention include, but are not limited to the following: histidine, histidine salts, such as histidine-HCl, histidine derivatives, including polyhistidine and histidine hydroxamate, arginine, lysine, tryptophan, methionine, arginine, glutamic acid, aspartic acid, glycine. The use of histidine-HCl is particularly preferred.

When used as a second BEC, amino acids or amino acid derivatives typically comprise at least about 1%, preferably, at least about 2%, by weight of the total composition. Preferably, the amino acid or amino acid derivative comprises not more than about 15%, preferably, not more than about 10%, by weight, of the total composition. In formulations comprising amino acids or amino acid derivatives, ST usually comprises at least about 10%, preferably at least about 20%, even more preferably, at least about 35%, by weight, of the total composition. Characteristically ST comprises not more than about 50%, preferably not more than about 46%, even more preferably, not more than about 44%, by weight, of the total composition. The most preferred non-aqueous injectable formulation preparation, having amino acids or amino acid derivatives, comprises amino acid or derivative in an amount of 0.05 to 0.3 mg (2–10% by weight) per mg of ST (35–44% by weight).

In another embodiment of the present invention the second BEC is a hydroxamate or hydroxamate derivative. Preferred hydroxamates for use as bioavailability-enhancing constituents in the present invention are those which bind metals, particularly, zinc, these include: suberohydroxamic acid, salicly hydroxamic acid, bufexamac acid, and caprylohydroxamic acid.

When used as a second BEC, an hydroxamate or an hydroxamate derivative typically comprise at least about 1%, preferably, at least about 2%, by weight, of the total composition. Preferably, the hydroxamate or hydroxamate derivative comprises not more than about 15%, preferably, not more than about 10%, by weight, of the total composition. In formulations comprising hydroxamates or hydroxamate derivatives, ST usually comprises at least about 10%, preferably at least about 20%, even more preferably, at least about 35%, by weight, of the total composition. Characteristically, ST comprises not more than about 50%, preferably not more than about 46%, even more preferably, not more than about 44%, by weight, of the total composition. The most preferred non-aqueous injectable formulation preparation, having hydroxamates or hydroxamate derivatives, comprises hydroxamate or hydroxamate derivatives in an amount of 0.05 to 0.3 mg (2–10% by weight) per mg of ST (35–44% by weight).

Another embodiment of the present invention provides for a composition comprising a non-reducing carbohydrate as the second BEC. Non-reducing carbohydrates which are useful in the compositions of the present invention include, but are not limited to: polyols and their ester derivatives. Polyols which are preferred for use in the present invention include, but are not limited to, trehalose, sucrose, mannitol and sorbitol. Trehalose (in the form of trehalose dihydrate) is particularly preferred. Preferred polyol esters include: acetate, octaacetate, and octasulfate polyol esters. Particularly preferred polyol esters include trehalose octaacetate, sucrose octaacetate, and cellobiose octaacetate.

When used as a second BEC, non-reducing carbohydrates typically constitute at least about 1%, more preferably, at least about 3%, by weight, of the total composition. Typically the non-reducing carbohydrate comprises not more than about 20%, preferably, not more than about 15%, by weight, of the total composition. In formulations comprising non-reducing carbohydrates, ST typically constitutes at least about 10%, preferably, at least about 20%, even more typically, at least about 35% , by weight of the composition; but usually not more than about 50%, preferably, not more than about 46%, even more typically, not more than about 44%, by weight, of the total composition.

In another embodiment of the present invention the second BEC is an oxo-acid salt (where an oxo-acid is an acid in which the acidic hydrogen atoms are bound to oxygen atoms). Preferred second BECs of this embodiment include: (i) monobasic sodium phosphate, $NaH_2PO_4$, diabasic sodium phosphate, $Na_2HPO_4$, or a mixture of monobasic and diabasic; (ii) monobasic potassium phosphate, $KH_2PO_4$, diabasic potassium phosphate, $K_2HPO_4$, or a mixture of monobasic and diabasic; (iii) monobasic calcium phosphate, $Ca(H_2PO_4)_2$, diabasic calcium phosphate, $CaHPO_4$, or a mixture of monobasic and diabasic; (iv) various other phosphate, sulfate or nitrate salts such as $Ca_3(PO_4)_2$, $Na_2SO_4$, and $NaNO_3$, or mixtures thereof. In a preferred embodiment the second BEC is a mixture of monobasic- and diabasic sodium phosphate, in a mixture containing more monobasic than diabasic. It is important to note that as used in this embodiment and all the phosphate-containing, non-aqueous embodiments, the phosphate need not act as a buffering component, and typically does not affect the pH during the formulating of the composition.

When used as a second BEC, oxo-acid salts typically constitute at least about 1%, more preferably, at least about 2%, by weight, of the total composition. Typically the oxo-acid salt comprises not more than about 15%, preferably, not more than about 10%, by weight, of the total composition. In formulations comprising oxo-acid salts, ST typically constitutes at least about 10%, preferably, at least about 20%, even more typically, at least about 35%, by weight, of the composition; but usually not more than about 50%, preferably, not more than about 46%, even more typically, not more than about 44%, by weight, of the total composition.

The non-aqueous carrier (excipient) can be any substance that is biocompatible and liquid or soft enough at the animal's body temperature to release the somatotropin into the animal's bloodstream at a desired rate. The carrier is usually hydrophobic and commonly organic, e.g., an oil or fat of vegetable, animal, mineral or synthetic origin or derivation. Preferably, but not necessarily, the carrier includes at least one chemical moiety of the kind that typifies "fatty" compounds, e.g., fatty acids, alcohols, esters, etc., i.e., a hydrocarbon chain, an ester linkage, or both. "Fatty" acids in this context include acetic, propionic and butyric acids through straight- or branched-chain organic acids containing up to 30 or more carbon atoms. Preferably, the carrier is immiscible in water and/or soluble in the substances commonly known as fat solvents. The carrier can correspond to a reaction product of such a "fatty" compound or compounds with a hydroxy compound, e.g., a monohydric, di-hydric, trihydric or other polyhydric alcohol, e.g., glycerol, propanediol, lauryl alcohol, polyethylene or -propylene glycol, etc. These compounds include the fat-soluble vitamins, e.g., tocopherols and their esters, e.g., acetates sometimes produced to stabilize tocopherols. Sometimes, for economic reasons, the carrier may preferably comprise a natural, unmodified vegetable oil such as sesame oil, soybean oil, peanut oil, palm oil,.or an unmodified fat. Alternatively the vegetable oil or fat may be modified by hydrogenation or other chemical means which is compatible with the present invention. The appropriate use of hydrophobic substances prepared by synthetic means is also envisioned.

The compositions of this invention typically contain at least about 10%, preferably at least about 15%, and most commonly at least about 20% ST. In some systems, they may advantageously contain as much as about 38%, or even as much as about 50%, or more, ST.

Compositions of this invention may also comprise, in addition to the biocompatible oil, an "antihydration agent" which term as used herein means a substance that retards hydration of a somatotropin and/or the biocompatible oil or fat and thereby further decreases and/or stabilizes the rate of release of the ST from that composition following administration to an animal. A great variety of non-toxic antihydration agents are known. By way of example there are "gelling" agents which, when dispersed, and in some cases heated to dissolve them in the oil, give the body of oil greater visco-elasticity (and therefore greater structural stability) and thereby slow down penetration of the oil by body fluids.

The exact mechanism of these agents in the present invention is not fully understood. Thus it has been observed that certain known "gelling" agents provide the desired antihydration effect even when the oil containing such an agent has not been heated to enhance their gelling effect, or when the gel formation, once formed, has been substantially eliminated (e.g. by shear forces). Also, various antihydration agents that do not have substantial ability to gel the oil are suitable for use in this invention (magnesium stearate is one example).

Exemplary antihydration agents include various polyvalent metal salts or complexes of organic acids, for instance fatty acids having from about 8 (preferably at least about 10) to about 22 (preferably up to about 20) carbon atoms, e.g. aluminum, zinc, magnesium or calcium salts of lauric acid, palmitic acid, stearic acid and the like. Such salts may be mono-, di- or tri-substituted, depending on the valence of the metal and the degree of oxidation of the metal by the acid. Particularly useful are the aluminum salts of such fatty acids. Aluminum monostearate and distearate are particularly preferred anti-hydration agents. Others that are useful include aluminum tristearate, calcium mono- and distearate, magnesium mono- and distearate and the corresponding palmitates, laurates and the like. In many embodiments, the concentration of such an antihydration agent, based on the weight of the oil plus that agent, will be advantageously between about 1% and about 10% (most typically between about 2% and about 5%), although other concentrations may be suitable in some cases.

In one preferred embodiment the carrier is selected such that the composition is a thick and free-flowing suspension at 25° C.; e.g., approximately 95% sesame oil gelled with 5% aluminum monostearate (AlMS).

Dry, solid somatotropin and dry, solid bioavailability-enhancing constituent can be prepared by lyophilization of appropriate solutions containing, respectively the somatotropin or the BEC. Alternatively, ST or the BEC can be prepared by any other means which provides them in the proper form for use in the present invention.

Another embodiment of the present invention provides for a method of preparing the compositions of matter described above. The compositions of matter described for the instant invention may be prepared by any means or procedure that provides for a composition which delivers the desired enhanced bioavailability of ST at the desired levels. In a preferred embodiment of the invention a certain amount of the first BEC that is effective to further increase the bioavailability of bioactive ST is mixed with the non-aqueous excipient. Next, lyophilized ST is added and the mixture is milled for an appropriate period of time in order to achieve the desired particle size and viscosity of the composition (i.e., a particle size should be small enough to provide a viscosity which allows the formulation to be useful according to the current invention). A discussion of how to achieve the desired particle size may be found in U.S. Pat. No. 5,013,713 to James Mitchell, which is herein incorporated by reference for this purpose.

While the above method is preferred, the order of combining the first BEC and the ST is flexible. Similarly, the order of combining optional second BEC, the first BEC and the ST is flexible. Furthermore, ST and either or both of the BECs can be co-lyophilized and the co-lyophilized product can be mixed with the non-aqueous excipient and processed as described above.

Another embodiment of the instant invention provides for the parenteral administration, to a susceptible animal, of a composition, as described supra, so as to produce increased weight gain, enhanced milk production, or any other desirable physiological response, produced by increased serum levels of somatotropin.

The parenteral administration of the formulations, described herein, to a susceptible animal (e.g., a mammal such as a bovine), has shown that the compositions exhibit surprisingly improved bioavailability performance characteristics for ST when compared to previously available ST formulations.

In particular, the described compositions provide a relatively more rapid, yet controlled, release during the first several days after administration without the early release becoming an exaggerated "burst" to the extent that durability of the release is unduly impaired. Typically, in terms its practical effects, the most meaningful measure of the ST release over a given period of time is calculated as the area under the curve ("AUC") illustrating the amount of ST made available by the release (e.g., the serum level of ST in the animal) and/or a physiological consequence of the release (e.g., milk produced or weight gained by an animal in which the ST has been released). Use of the invention has been found to provide a surprisingly greater AUC for measured serum concentrations, this finding is particularly true for periods of time of 14 days or more.

Accordingly it is expected that when the AUC represents the desirable physiological effects of ST release (e.g., the amount of milk produced daily by bovine or other lactating animals) for animals that would be treated with the ST formulations of the present invention, the AUC would be not only greater than those of known ST/oil formulations, but also greater than would be expected, given the magnitude of the serum ST levels present in the lactating animal. Put another way, this means that the formulations of the present invention not only provide for an enhanced release of ST, but also increase the efficacy of the released amount of ST formulation. Consequently, despite declining serum ST levels, it is expected that increased milk production would be sustained at a level which is high.

Examples of the enhanced physiological effects produced by compositions of the present invention are described in examples 1–7 below. These examples describe the unexpected results of increased blood serum levels or mature rodent weight gain response in animals treated with the ST compositions of the instant invention. In these examples serum ST levels and body weight of animals injected with the compositions of the present invention are compared with the same parameters in animals, that were either un-treated, or were injected with the same dose of the same somatotropin in a composition which comprised essentially the same carrier, but which lacked the bioavailability-enhancing constituent(s). These examples demonstrate that the animals injected with the ST compositions of the present invention would have a high and sustained level of milk production.

Thus the compositions of the instant invention provide both higher serum ST levels and increased rate of weight gain per milligram of ST injected, than provided by previously know compositions. It is believed that when administered to lactating cows, the instant inventions also provide a more sustained elevated milk production response, per milligram of ST injected, than provided by previously know compositions.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Although many of the exemplary embodiments herein discuss a 14-day injection cycle is to be understood that other intervals between injections may often be desirable and apply equally well under different or the same animal environmental conditions. Such other exemplary injections cycles include by way of non-limiting examples intervals ranging from 10-day injection cycles to 28-day injection cycles, as well as day intervals in between and outside of those ranges and exemplary injections cycles of increasing or decreasing intervals.

Example 1

Examples of Representative Compositions

Table 1 provides a tabulated summary of exemplary compositions for enhanced bioavailability of ST formulations. The weight percent of the bioavailability-enhancing factor and somatotropin are indicated as is the non-aqueous excipient used.

TABLE 1

| 1st BEC | % 1st BEC | 2nd BEC | % 2nd BEC | % ZnbST[1] | Hydrophobic Carrier[2] |
|---|---|---|---|---|---|
| Tween ® 80 | 0.5 | — | — | 38 | SO:AlMS 95:5 |
| Tween ® 80 | 0.5 | — | — | 43 | SO:AlMS 95:5 |
| Tween ® 80 | 1 | — | — | 40.5 | SO:AlMS 95:5 |
| Tween ® 80 | 1 | — | — | 40.5 | SO:AlMS 95:5 |
| Tween ® 80 | 2 | — | — | 38 | SO:AlMS 95:5 |
| Tween ® 80 | 2 | — | — | 43 | SO:AlMS 95:5 |
| Hydroxypropyl beta cyclodextrin | 5 | — | — | 38 | SO:AlMS 95:5 |
| Octylglucoside | 2 | — | — | 38 | SO:AlMS 95:5 |
| Sucrose distearate | 5 | — | — | 38 | SO:AlMS 95:5 |
| Sucrose stearate | 5 | — | — | 38 | SO:AlMS 95:5 |
| Polyoxyethylene 8 stearate | 2.5 | — | — | 38 | SO:AlMS 95:5 |
| Polyoxyethylene 8 stearate | 5 | — | — | 39 | SO:AlMS 95:6 |
| Polyoxyethylene 50 stearate | 5 | — | — | 38 | SO:AlMS 95:5 |
| Polyoxyethylene 100 stearate | 5 | — | — | 38 | SO:AlMS 95:5 |
| Polyethylene glycol 20 glyceride | 5 | — | — | 38 | SO:AlMS 95:5 |
| Pluronic ® F108 | 2 | — | — | 38 | SO:AlMS 95:5 |
| Tocopherol polyethylene glycol 1000 succinate | 2 | — | — | 38 | SO:AlMS 95:5 |
| Tween ® 80 | 0.25 | NaP(mono:di = 6:4) | 5 | 38 | SO:AlMS 95:5 |
| Tween ® 80 | 0.5 | NaP(mono:di = 6:4) | 2 | 38 | SO:AlMS 95:5 |
| Tween ® 80 | 0.5 | NaP(mono:di = 6:4) | 5 | 38 | SO:AlMS 95:5 |
| Tween ® 80 | 0.5 | NaP(mono:di = 6:4) | 8 | 38 | SO:AlMS 95:5 |
| Tween ® 80 | 1 | NaP(mono:di = 6:4) | 2 | 38 | SO:AlMS 95:5 |
| Tween ® 80 | 1 | NaP(mono:di = 6:4) | 5 | 38 | SO:AlMS 95:5 |
| Tween ® 80 | 0.5 | Trehalose Octaacetate | 5 | 38 | SO:AlMS 95:5 |
| Tween ® 80 | 0.5 | Sucrose Octaacetate | 5 | 38 | SO:AlMS 95:5 |
| Polyoxyethylene 8 stearate | 2.5 | NaP(mono:di = 6:4)[3] | 5 | 36 | SO:AlMS 95:5 |
| Polyoxyethylene 8 stearate | 5 | NaP(mono:di = 6:4) | 5 | 36 | SO:AlMS 95:6 |
| Polyoxyethylene 8 stearate | 5 | NaP(monobasic) | 5 | 36 | SO:AlMS 95:7 |
| Polyoxyethylene 8 stearate | 5 | Trehalose | 10 | 34 | SO:AlMS 95:8 |
| Polyoxyethylene 8 stearate | 5 | Histidine-HCl | 3 | 36 | SO:AlMS 95:9 |

[1]ZnbST = Zinc bound bovine somatotropin.
[2]SO:AlMS 95:5 = sesame oil (95%):aluminum monostearate (5%)
[3]NaP (6:4) = a 6 to 4 molar ratio mixture of the monobasic to dibasic form of the sodium phosphate salt

Example 2

Rat Growth Studies in Rodents for a Variety of Compositions

A rat growth assay was used to measure the biological potency of ST containing formulations. As used here the term "biological potency" denotes the capacity of the ST formulations to accelerate weight gain in rodents treated therewith.

Rodents were injected subcutaneously with 25 mg of bST mixed with the various BECs described in Table 2 and the rodent daily weights were followed for 15 days. Table 2 lists the formulation, the relative potency (versus POSILAC®), and the 95% confidence interval for relative potency.

TABLE 2 bST formulation relative potency in rodents

| Description of Composition All in SO/Alms[1] | Relative Potency | Lower Limit | Higher Limit |
|---|---|---|---|
| 38% ZnbST + 0.5% Tween ® 80 | 119.0 | 107.1 | 130.8 |
| 43% ZnbST + 0.5% Tween ® 80 | 125.0 | 113.7 | 136.2 |
| 40.5% ZnbST + 1% Tween ® 80 | 120.4 | 109.2 | 131.5 |
| 38% ZnbST + 2% Tween ® 80 | 114.5 | 99.2 | 129.8 |
| 43% ZnbST + 2% Tween ® 80 | 111.7 | 100.2 | 123.3 |
| 38% ZnbST + 5% Hydroxypropyl beta cyclodextrin | 133.3 | 100.6 | 166.0 |
| 38% ZnbST + 5% sucrose stearate | 114.3 | 100.3 | 128.4 |
| 38% ZnbST + 5% Polyoxyethylene 8 stearate | 114.3 | 99.5 | 129.2 |
| 38% ZnbST + 5% Polyoxyethylene 50 stearate | 121.2 | 105.4 | 137.0 |
| 38% ZnbST + 5% Polyoxyethylene 100 stearate | 104.3 | 90.5 | 118.1 |
| 38% ZnbST + 5% Tocopherol polyethylene glycol 1000 succinate | 104.8 | 93.6 | 116.0 |
| 38% ZnbST + 0.25% Tween ® 80 + 5% NaP(6:4)[2] | 108.5 | 101.1 | 115.8 |
| 38% ZnbST + 0.5% Tween ® 80 + 2% NaP(6:4) | 122.4 | 114.2 | 130.7 |
| 38% ZnbST + 1% Tween ® 80 + 2% NaP(6:4) | 114.6 | 107.7 | 121.6 |

TABLE 2-continued bST formulation relative potency in rodents

| Description of Composition<br>All in SO/Alms[1] | Relative<br>Potency | Lower<br>Limit | Higher Limit |
|---|---|---|---|
| 38% ZnbST + 1% Tween ® 80 + 5% NaP(6:4) | 101.3 | 93.6 | 108.9 |
| 38% ZnbST + 0.5% Tween ® 80 + 5% Trehalose Octaacetate | 128.4 | 118.9 | 137.9 |

[1]SO/AlMS (2.5%) = sesame oil 95%:aluminum monostearate 5%
[2]NaP (6:4) = a 6 to 4 molar ratio mixture of the monobasic to diabasic form of the sodium phosphate salt.

Example 3

Efficacy of Formulations Comprising HPBC or POE4S as the First Bioavailability Enhancing Constituent The performance of the formulation in the animals which received an injection of this formulation was determined by measuring the concentration of bovine somatotropin (bST) in the animal's serum over time, and then calculating the area under the curve (AUC) for a concentration vs. time plot. These studies clearly demonstrated that the addition of hydroxypropyl beta cyclodextrin (HPBC) or polyoxyethylene 4 stearate (POE4S) to the formulation surprisingly improved the bST bioavailability, as measured by serum bST AUCs in animals such as rodents or calves and would do the same in dairy cows. The formulations also exhibited dramatic improvements as measured by weight gain response in rodents and it is expected would exhibit the dramatic improvements by increased milk production in dairy cows when administered to the same.

The performance improvement of the formulation when compared with the control is illustrated by two lots shown in FIG. 1. Lot NBP6224525-C contains 42% (dry solid) Zinc bovine somatotropin (ZnbST) and 5% (dry solid) hydroxypropyl beta cyclodextrin (HPBC), and lots NBP6224525-B contain 38% (dry solid) ZnbST and 5% (dry solid) polyoxyethylene 4 stearate (POE4S). Both are suspended in the typical POSILAC® excipient, i.e., 95% sesame oil gelled with 5% aluminum monostearate (AIMS).

For the present example, all bST formulations were or would be administered subcutaneously. The dosage for pharmacokinetic studies in rodents is or would be 15 mg of bST. For the calf studies the dosage was or would be 500 mg bST.

The mean bST serum concentrations in rodents receiving these formulations are measured over a 14 day period and are shown in FIG. 1. Compared to POSILAC®, a surprisingly elevated serum bST concentration was observed with the formulations containing HPBC and POE4S.

As shown in FIG. 1, concentration of serum bST increased over both POSILAC® and the negative control after injection of the suspension formulations in rodents. Over 14-day cycle, the relative bST AUC (the HPBC or POE4S formulation AUC/POSILAC® AUC) is calculated to be 1.37 for HPBC and 1.17 for POE4S, indicating that the presence of the first BEC in the formulation dramatically improves the bST release into the circulatory system and results in a bST increase in bioavailability compared with POSILAC®.

Example 4

Figure 2:
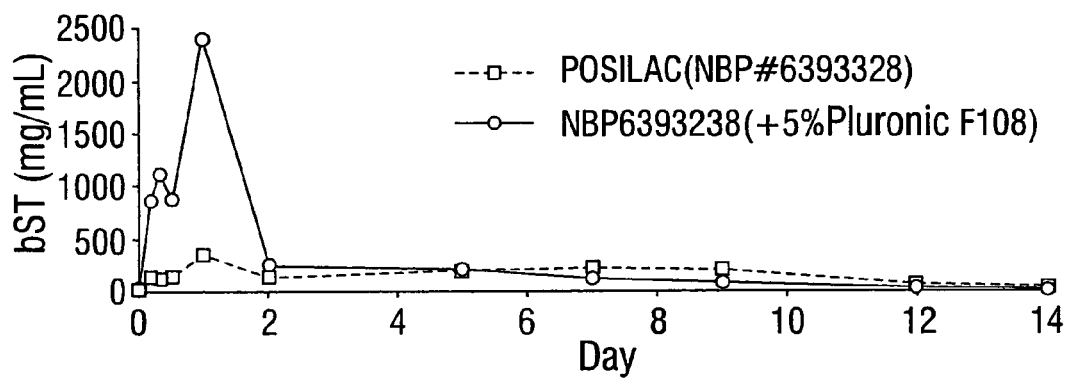
FIG. 2 is a graph showing a control treatment or example with no BEC added to the bST, and an example measuring the serum bovine somatotropin ("bST") levels over time in rodents treated with a bST composition which contained Pluronic® 108 as a first BEC.

Efficacy of Formulations Comprising Pluronic® F108 as the first Bioavailability Enhancing Constituent The mean bST serum concentrations over 14 days in rodents after receiving the Pluronic® F108 formulation (a polyoxyethylene-polyoxypropylene copolymer comprising approximately 80% polyoxyethylene, by weight, and with an average molecular weight of approximately 3000 which is available from BASF Corporation, Toronto, Ontario, Canada) Lot NBP 6393238 are shown in FIG. 2. Compared to a control treatment with no BEC added to the bST, an elevated serum bST concentration has been observed with the Pluronic® F108 formulation. Over a 14 day cycle, the presence of Pluronic® F108 in the suspension formulation has improved the bST bioavailability 1.76 times more than POSILAC®.

Example 5

Figure 3:
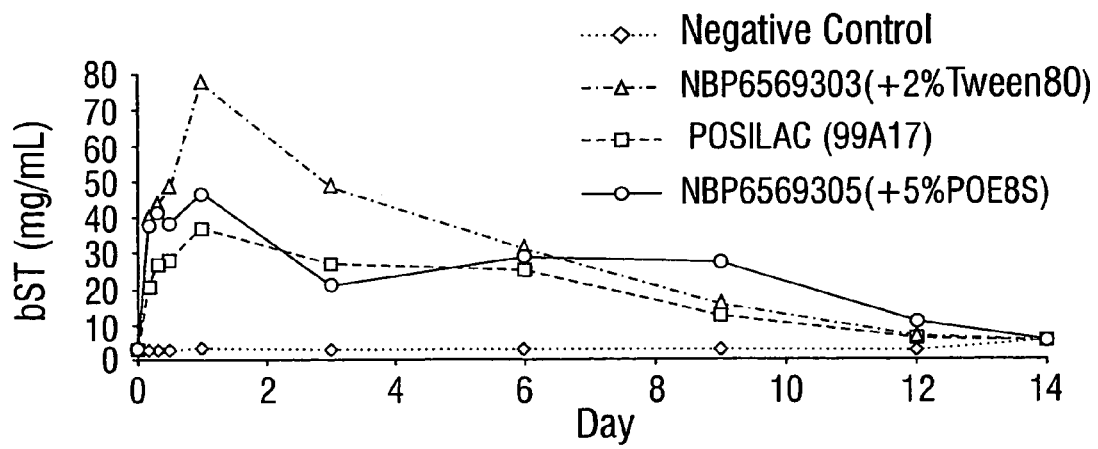
FIG. 3 is a graph showing a control treatment or example with no BEC added to the bST, and two examples measuring the serum bST levels over time in calves treated with a bST composition which contained in one example Tween® 80 (polyoxyethylene(20) sorbitan monooleate) as a BEC, and in the other example, polyoxyethylene 8 stearate (POE8S) as a BEC.

Efficacy of Formulations Comprising POE8S or Tween® 80 as the first Bioavailability Enhancing Constituent The mean bST serum concentrations over 14 days in calves after receiving the polyoxyethylene 8 stearate (POE8S) or the Tween® 80 formulation are shown in FIG. 3. Compared to POSILAC®, the presence of the first BEC in the suspension formulation has improved the bST release into the circulatory system. The relative bST AUC (the BEC formulation AUC/POSILAC® AUC) is calculated to be 1.28 and 1.58 for the POE8S and Tween® 80 formulation, respectively. Furthermore, the POE8S formulation demonstrates a surprising improvement in bST release duration: the circulating bST concentrations remain above the baseline at day 12 post injection. These data demonstrate a surprisingly prolonged release for the animals treated with the formulations containing POE8S.

Particularly surprising is the observation that the improved response would be sustained, in animals treated with the first BEC-containing ST formulations, despite the fact that the serum bST levels for animals treated with the POSILAC® formulation, or the negative control, are nearly identical at the end of each 14-day. These data demonstrate a surprisingly prolonged response for the animals treated with the formulations containing POE8S as the first BEC.

Example 6

Efficacy of Formulations Comprising a First BEC and a Second BEC.

Formulations comprising bST and both a first BEC and an optional second BEC have been found to provide surprisingly elevated release of bST in laboratory rodents, as measured by a) increased serum bST levels in the animals; and b) resulting weight gains in rodents, and c) would be expected in cattle to produce elevated milk production, for over 14 days after administration.

Figure 4:
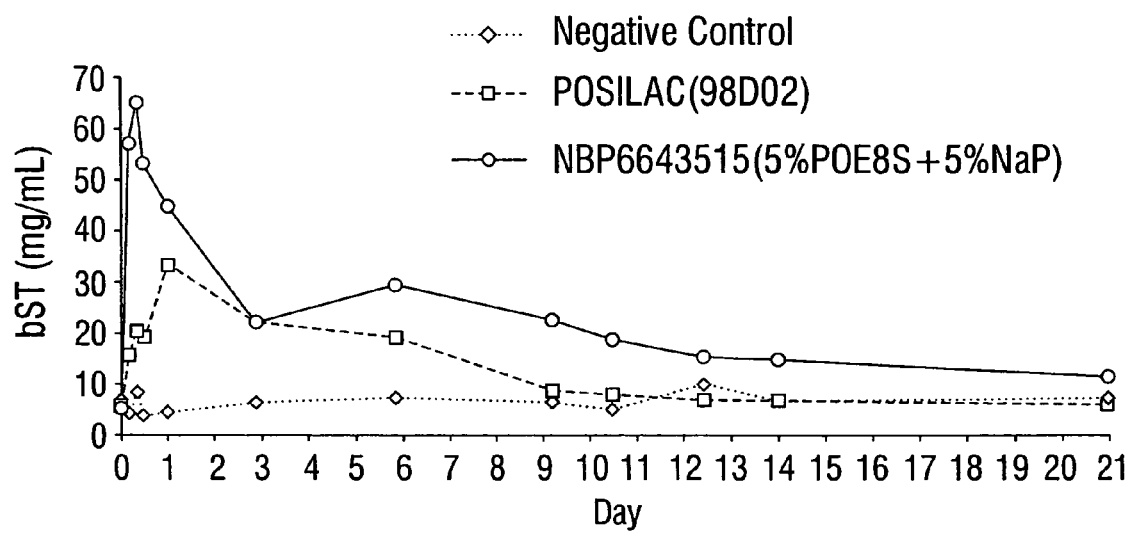
FIG. 4 is a graph showing two control treatments, one with no bST, the second control having no BEC added to the bST, and one exemplary embodiment of the invention having both a first and a second BEC, as shown by measuring the serum bST levels over time in calves. The first BEC in the exemplary embodiment being polyoxyethylene 8 stearate (POE8S) and having sodium phosphate (NaP) as the second BEC.
Figure 5:
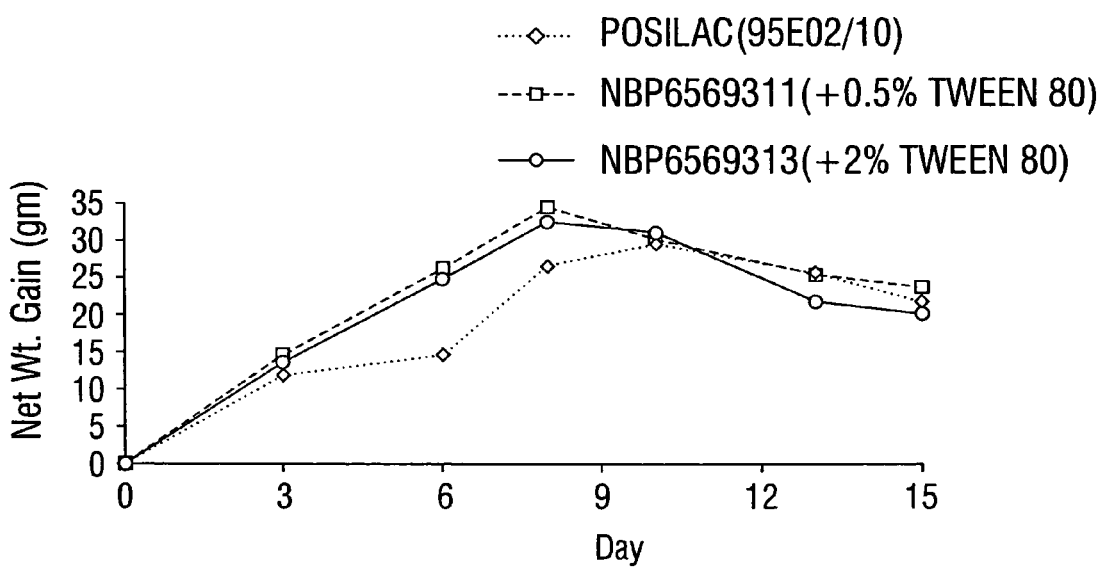
FIG. 5 is a graph showing weight gain over time in mature female rodents treated with two bST compositions which contained different levels of Tween® 80 as the first BEC.
Figure 6:
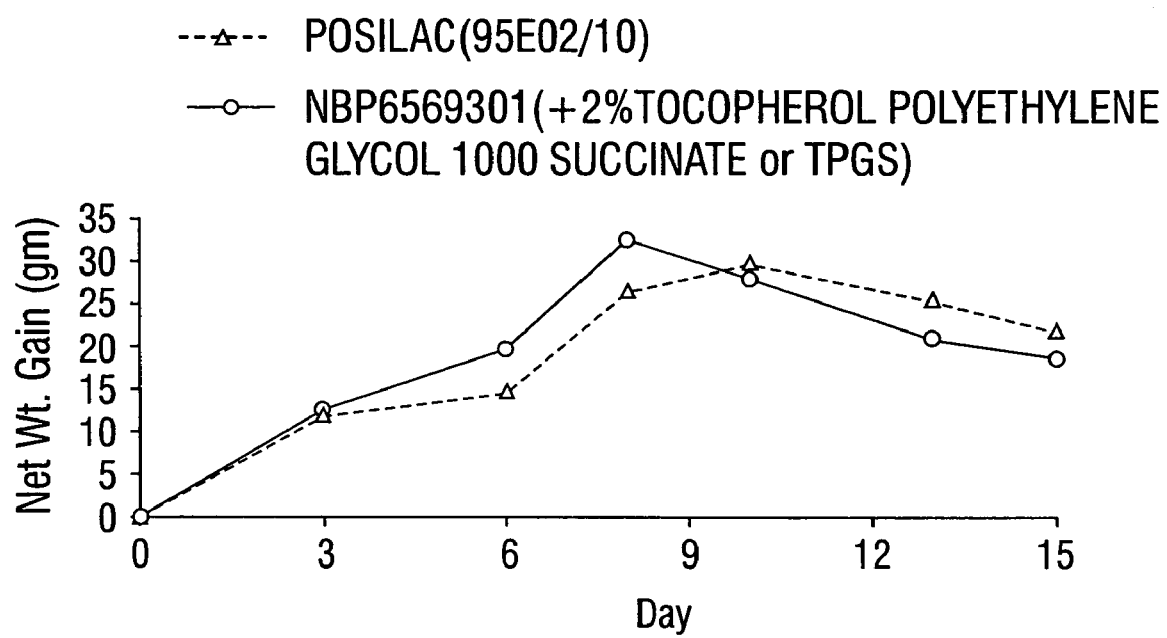
FIG. 6 is a graph showing weight gain over time in mature female rodents treated with a bST composition which contained tocopherol polyethylene glycol succinate (TPGS) as the first BEC.

The calf serum ST performance improvement of the formulations containing both a first BEC and an optional second BEC of the instant invention, when compared with a bST control and a negative control, is illustrated in FIG. 4. The rodent weight gain performance improvement of the formulations containing both a first BEC and a second BEC of the instant invention, when compared with a bST control, is shown in Table 2.

The dosages of bST administered were the same as those described in the other Examples. The mean bST serum concentrations over 14 days in calves after receiving formulations when compared to POSILAC®, show surprising and a remarkably sustained and elevated serum bST concentration in animals treated with formulations containing both a first BEC and an optional second BEC as can be seen, for example, in FIG. 4.

Example 7

Efficacy of Formulations Comprising POE8S as a First BEC, and a Sodium Phosphate Salt as a Second BEC Serum bST levels in an animal that has received an injection of enhanced bST formulations containing POE8S as the first BEC, and an oxo-acid salt as the second BEC were determined by measuring the animal's serum bST concentrations over time and then calculating the area under the curve (AUC) for a concentration vs time plot. Addition of certain salts of oxo-acids or amino acid or non-reducing carbohydrate as the second BEC has shown surprisingly improved results with respect to the bST bioavailability in formulations comprising a first BEC comprising one or more compounds selected from the group consisting of polyoxyethylene fatty acids esters, cyclodextrins, poloxamers, polyoxyethylene sorbitan fatty acid esters, tocopherol polyethylene glycol succinates, sugar fatty acid esters, polyoxyethylene glycerides, and polyoxyethylene vegetable oils, as measured by serum bST AUCs in animals such as calves. Also improved was the performance of the formulation in rodents as measured by weight gain response and the same improved performance is expected in dairy cows as measured by milk production.

The improvement in performance of the bST/first BEC/second formulations when compared with POSILAC® is illustrated by lot NBP 6643515. The lot contains 38% (dry solid) zinc bovine somatotropin (ZnbST), 5% POE8S (waxy solid) and 5% (dry solid) sodium phosphate (at 6:4 molar ratio of monobasic to diabasic) in the typical POSILAC® excipient, i.e., 95% sesame oil gelled with 5% aluminum monostearate (AIMS). The relative bST AUC (bST/POE8S/oxo-acid BEC formulation AUC over POSILAC® AUC) is calculated to be 1.67.

The dosages of bST administered were the same as those described in Example 3. The mean bST serum concentrations in calves were measured over a 21-day period after receiving the formulation, these are shown in FIG. 4. When compared to both the bST and negative control, a surprisingly sustained and elevated serum bST concentration has been observed with these formulations. Notably, the bST/POE8S/oxo-acid formulation in FIG. 4 showed surprising and unexpected results up to day 21 in terms of extended response above baseline. It is expected that the surprising and unexpected extended response would continue beyond day 21 as well.

It is expected that the concentration of serum bST concentration in dairy cows injected with the bST/POE8S/oxo-acid salt formulation would be increased with respect to both POSILAC® and the negative control. Over 14-day or 21 day or other selected injection interval, the expected relative bST AUC (the new formulation AUC over POSILAC® AUC) would indicate that the presence of POE8S and sodium phosphate salt mixture in the formulation would enhance the bST release into the circulatory system and would result in a large increase in bST bioavailability in target animals when compared to POSILAC®.

Following injection of the bST/POE8S/oxo-acid containing formulation, milk production would increase and continue to be elevated with respect to both POSILAC® and the negative control throughout each injection cycle. The increase in overall milk yield, over 14-day or 21-day or other selected injection cycles, would be greater than that of lactating cattle treated with POSILAC®.

Example 8

Pharmacokinetic Studies in Rodents for a Variety of Compositions

Rodents were injected subcutaneously with 15 mg of bST (mixed with the various BEC's described in Table #1) according to the following protocol.

Test Subjects
  Mature female Sprague-Dawley rats, 12–13 weeks of age, ~250 g.

Control Group:
  Six (6) rats treated with reference standard material.

Treated Groups:
  Six (6) rats per test article (formulation lot), randomly assigned. Animals were assigned to treatment groups using a completely randomized design according to body weight on Day −1 or Day 0 prior to treatment initiation. A weight range of 250+/−20 gram was used.

Test Articles:
  POSILAC®, as a positive control, and various bST formulations were studied.

Section B: Weighing, Dosing, Blood Collection, and Sample Shipment

Weighing:

Animals were weighed on Day −1 or Day 0 for randomization and treatment assignment. A final weight was taken on Day 14 following the final blood sample collection.

Route of Injection:

Subcutaneous (SC) injection in the dorsal suprascapular region. Injections were administered with 1 cc tuberculin syringes with 18 G 1.5-inch needles for all formulations.

Dose Volumes 15 mg of bST with the dose volume of ~0.04 ml were administered to each rat on Day 0. A fill volume of ~0.08 ml was prepared to adjust for the amount of formulation remaining in the needle following the injection. The time of injection was recorded for each individual rat. Syringes were weighed both prior to and following injection to determine the weight of the protein injected.

Blood Collection:

Blood samples were collected via retro-orbital bleeds, using alternating eyes at the various time-points, following anesthesia with $CO_2/O_2$ (80/20) gas. EDTA coated or non-coated micro-hematocrit capillary tubes were used for the blood collections. The whole blood was transferred to blood plasma separator tubes (Microtainer® with EDTA, lavender; MFG# BD5960). The blood was then centrifuged at 6000g for 10 minutes at room temperature. Samples were stored frozen at −20° C.

Blood Volumes:

It was necessary to obtain a minimum of 200 μl of whole blood at each time point from each rat in order to have 100 μl of plasma. A total volume of 300 μl of whole blood is preferable to ensure an adequate plasma volume.

Blood Collection Time Points:

Blood samples were collected at 11 time points, 7 different time points for each rat, following the sampling scheme outlined in the Rat Blood Sampling Schedule (below). The time of collection were recorded for each individual rat.

Blood Collection Time Points
Day 0, prior to injection
4, 8, and 12 hours post-injection (after the injection)
Day 1 (24 hr)
Day 2 (48 hr)
Day 5 (120 hr)
Day 7 (168 hr)
Day 9 (216 hr)
Day 12 (288 hr)
Day 14 (336 hr)
Note: All blood collections were within+/−one (1) hour.

Rat Blood Sampling Schedule:

| Time | Rat # 1 | 2 | 3 | 4 | 5 | 6 |
|---|---|---|---|---|---|---|
| 0 | X | X | X | X | X | X |
| 4 hr | X |   | X |   | X |   |
| 8 hr | X | X |   | X |   |   |
| 12 hr |   | X | X |   |   | X |
| Day 1 (24 hr) |   |   |   | X | X | X |
| Day 2 (48 hr) | X | X | X |   |   |   |
| Day 5 (120 hr) |   | X |   | X | X | X |
| Day 7 (168 hr) | X |   | X | X | X |   |
| Day 9 (216 hr) |   | X |   | X |   | X |
| Day 12 (288 hr) | X |   | X |   | X | X |
| Day 14 (336 hr) | X | X | X | X | X | X |

Note:
This scheme gives seven (7) bleeds per rat over a 14 day period.

Serum samples were collected and analyzed for bST levels.

All of the compositions and methods disclosed and claimed herein can be made and executed without undue experimentation in light of the present disclosure. While the compositions and methods of this invention have been described in preferred embodiments, it will be apparent to the skilled artisan that variations may be applied to the compositions and methods and in the steps or in the sequence of steps of the methods described herein without departing from the concept, spirit and scope of the invention. Further, it will be apparent that certain agents which are both chemically and physiologically related may be substituted for the agents specifically mentioned herein provided the same or similar results are obtained. All such similar substitutes and modifications that are reasonably apparent to those skilled in the art are within the spirit, scope and concept of the invention as defined by the appended claims.

REFERENCES

The following references, to the extent that they provide exemplary procedural or other details supplementary to those set forth herein, are specifically incorporated herein by reference.

Christensen et al., WO 97/03692; February/1997; A61K 38/27, 33/30
Dong et al., WO 00/13674; March/2000;A61K 9/20, 9/48
Ewuribe, U.S. Pat. No. 5,359,030; October/1994; 530/303
Ewuribe, U.S. Pat. No. 5,438,040; August/1995; 514/3
Ewuribe, U.S. Pat. No. 5,681,811;October/1997; 514/8
Furguson et al., U.S. Pat. No. 4,977,140; December/1990; 514/12
Hamilton et al., U.S. Pat. No. 4,816,568; March/1989; 530/399
Kim et al., U.S. Pat. No. 5,520,927; May/1996; 424/450
Kim et al., U.S. Pat. No. 5,744,163; April/1998; 424/489
Krivi, G.G., U.S. Pat. No. 5,399,489; March/1995; 435/172.3
Magruder et al., U.S. Pat. No. 5,034,229; July/1991; 424/422
Martin, EP 0 216 485; April/1987; C 07 G 15/00
Mitchell, U.S. Pat. No. 5,739,108; April/1998; 514/12
Pikal et al., U.S. Pat. No. 5,612,315; March/1997; 514/21
Raman et al., U.S. Pat. No. 5,356,635; October/1994; 424/484
Raman et al., WO 93/13792; July/1993
Seeley et al., WO 93/19773; October/1993

Sivaramakrishnan et al., U.S. Pat. No. 5,219,572; June/1993; 424/438
SØrensen et al., WO 93/12812; July/1993; A61K 37/36
SØrensen et al., U.S. Pat. No. 5,849,704; December/1998; 514/12
Steber et al., EP 0 523 330 A1; January/1993; A61K 9/00
Storrs et al., U.S. Pat. No. 5,986,073; November/1999; 530/419
Tyle, U.S. Pat. No. 4,857,506; August/1989; 514/12
Viswanathan et al., U.S. Pat. No. 4,917,685; April/1990; 604/891.1

What is claimed is:

1. A method for sustaining elevated milk production response in a lactating mammal comprising:
   parenterally administering to the mammal a biocompatible composition of matter comprising:
   a) a somatotropin, active in the mammal;
   b) a first bioavailability enhancing constituent (BEC); and,
   c) optionally, a second BEC;
   wherein the first BEC is a non-ionic surfactant;
   wherein the second BEC is selected from one or a mixture of two or more of the following: one or more non-reducing carbohydrate(s) and one or more oxo-acid salt(s);
   wherein the somatotropin and BEC are suspended in a substantially non-aqueous hydrophobic carrier; wherein the somatotropin is present at from about 10% to about 50% by weight of the composition; wherein the first (BEC) is present at from about 0.1% to about 10% by weight of the composition; and, wherein the composition is fluidly injectable at 25 C.

2. The method of claim 1, wherein the first BEC comprises one or a mixture of two or more of the following: polyoxyethylene 4 stearate, polyoxyethylene 8 stearate, and polyoxyethylene(20) sorbitan monooleate (Tween® 80).

3. The method of claim 1, wherein the first BEC comprises polyethyleneoxide 8 stearate (POE8S).

4. The composition of claim 3, wherein the POE8S is present at a concentration of from about 0.1 to about 10%, by weight, of the composition.

5. The composition of claim 3 comprising a second BEC selected from one or a mixture of two or more of the following: trehalose, monobasic sodium phosphate, and mixture of monobasic- and dibasic-sodium phosphate in about a 6:4 molar ratio.

6. The method of claim 1 wherein the non-ionic surfactant is selected from one or a mixture of two or more of the following: polyoxyethylene fatty acids esters, poloxamers, polyoxyethylene sorbitan fatty acid esters, tocopherol polyethylene glycol succinates, sugar fatty acid esters, polyoxyethylene glycerides, and polyoxyethylene vegetable oils.

7. The method of claim 1 wherein the somatotropin is present as a zinc salt or complex.

8. The method of claim 1 wherein the somatotropin is bovine somatotropin.

9. The method of claim 1 comprising a second bioavailability enhancing constituent that is a non-reducing carbohydrate selected from one or a mixture of two or more of the following: at least one polyol and at least one carbohydrate ester.

10. The method of claim 9 wherein the second bioavailability enhancing constituent is selected from one or a mixture of two or more of the following: trehalose, sucrose, mannitol, sorbitol, trehalose octancetate, trehalose dihydrate, sucrose octaacetate, and cellobiose octaacetate.

11. The method of claim 10 wherein the first BEC is present at from about 0.1% to about 10%, by weight, of the composition and the second BEC is present at from about 1% to about 20%, by weight, of the composition.

12. The method of claim 11 wherein the somatotropin is bovine somatotropin present at about 10–50%, by weight, of the composition, and wherein the substantially non-aqueous hydrophobic carrier comprises about 95% sesame oil and about 5%, by weight, aluminum monostearate.

13. The method of claim 1 wherein the second bioavailability enhancing constituent (BEC) is selected from one or a mixture of two or more oxo-acid salt(s).

14. The method of claim 13 wherein the second BEG is selected from one or a mixture of two or more of the following: monobasic potassium phosphate, dibasic potassium phosphate, monobasic calcium phosphate, dibasic calcium phosphate, sodium nitrate, and dibasic sodium sulfate.

15. The method of claim 14 wherein the first BEC is present at from about 0.1% to about 10%, by weight, of the composition and the second BEC is present at from about 1% to about 15%, by weight, of the composition.

16. The method of claim 15 the somatotropin is bovine somatotropin present at about 10–50% and wherein the substantially non-aqueous hydrophobic carrier is comprised of about 95% sesame oil and about 5%, by weight, aluminum monostearate.

* * * * *

UNITED STATES PATENT AND TRADEMARK OFFICE
CERTIFICATE OF CORRECTION

| | | |
|---|---|---|
| PATENT NO. | : 7,037,516 B2 | Page 1 of 1 |
| APPLICATION NO. | : 10/792992 | |
| DATED | : May 2, 2006 | |
| INVENTOR(S) | : Yunhua N. Jeng and Kanaiyalal R. Patel | |

It is certified that error appears in the above-identified patent and that said Letters Patent is hereby corrected as shown below:

Column 25, Claim 1, Line 32, after "25" add the degree symbol --°--.

Column 25, Claim 4, Line 39, delete "composition" and insert -- method--.

Column 25, Claim 5, Line 42, delete "composition" and insert --method--.

Column 26, Claim 10, Line 17, delete "octancetate" and insert --octaacetate--.

Column 25, Claim 14, Line 32, delete "BEG" and insert --BEC--.

Signed and Sealed this

Twenty-sixth Day of June, 2007

JON W. DUDAS
*Director of the United States Patent and Trademark Office*